United States Patent

Schonert et al.

(10) Patent No.: US 6,173,717 B1
(45) Date of Patent: Jan. 16, 2001

(54) HAIR SHAPING METHOD USING ACIDIC AQUEOUS INTERMEDIATE RINSE TO PREVENT OVERCURLING

(75) Inventors: Dieter Schonert, Reinheim; Beate Dannecker, Darmstadt; Günther Lang, Reinheim; Dieter Hoch, Pfungstadt/Eich, all of (DE); Wilfried K. Kalbacher, Sao Paulo; Johann Markl, Rio de Janeiro, both of (BR)

(73) Assignee: Wella Aktiengesellschaft, Darmstadt (DE)

( * ) Notice: Under 35 U.S.C. 154(b), the term of this patent shall be extended for 0 days.

(21) Appl. No.: 09/355,655
(22) PCT Filed: Dec. 9, 1998
(86) PCT No.: PCT/EP98/08017
§ 371 Date: Aug. 2, 1999
§ 102(e) Date: Aug. 2, 1999
(87) PCT Pub. No.: WO99/32067
PCT Pub. Date: Jul. 1, 1999

(30) Foreign Application Priority Data

Dec. 19, 1997 (DE) .............................................. 197 56 654

(51) Int. Cl.[7] ..................................................... A45D 7/04
(52) U.S. Cl. ........................................... 132/202; 132/205
(58) Field of Search .................................. 132/204, 205, 132/206, 208, 209, 200; 8/432, 406, 563, 587; 424/70.4, 70.5, 70.51

(56) References Cited

U.S. PATENT DOCUMENTS

| | | | |
|---|---|---|---|
| 3,768,490 | * 10/1973 | Kalopissis et al. | 132/204 |
| 4,470,423 | * 9/1984 | Wajaroff | 132/204 |
| 4,770,872 | * 9/1988 | Hsiung et al. | 424/72 |
| 4,982,749 | * 1/1991 | Baker et al. | 132/204 |
| 4,996,997 | * 3/1991 | Williams et al. | 132/204 |
| 5,046,515 | * 9/1991 | Heinz et al. | 132/204 |
| 5,570,708 | * 11/1996 | Samain | 132/205 |
| 5,655,552 | * 8/1997 | Samain | 132/205 |
| 5,942,009 | * 8/1999 | Burns | 8/432 |

FOREIGN PATENT DOCUMENTS

8775 IV a/30h U 10/1956 (DE) .
36 10 394 A1 10/1987 (DE) .

OTHER PUBLICATIONS

"Ein Einfach Test Zur Pruefung Der Effizienz Des Spuelens Nach . . . " by D. Schwoeppe, E. Heymann, Sofw–Journal, 123, Feb. 1997, pp. 79–83.

* cited by examiner

Primary Examiner—Pedro Philogene
(74) Attorney, Agent, or Firm—Michael J. Striker

(57) ABSTRACT

Methods of permanent shaping and volumizing hair that are gentle and prevent overcurling are described. In one method using curlers to curl the hair, an alkaline permanent shaping composition having a pH of 7.6 to 11 and including a hair keratin-reducing substance is applied to the hair and allowed to act on the hair for 5 to 30 minutes at room temperature or for 2 to 20 minutes at an elevated temperature. Then the hair is optionally rinsed with water and subsequently with an acidic aqueous intermediate rinse, which has a pH of 2 to 6.5 and includes an aliphatic organic acid. Next the hair is wound onto curlers, after which the hair is allowed to rest for 30 minutes at room temperature or 20 minutes at an elevated temperature. After the resting period the hair is treated with an oxidant-based fixative, which can be a solution of hydrogen peroxide, and the curlers are removed. The hair is subsequently rinsed with water or washed with a shampoo to remove the fixative and combed into a hair style. For methods of uncurling hair the method is similar, but the step of winding on curlers is replaced by a step of combing the hair out and the acidic aqueous intermediate treating agent is in the form of a gel, cream or paste.

30 Claims, No Drawings

HAIR SHAPING METHOD USING ACIDIC AQUEOUS INTERMEDIATE RINSE TO PREVENT OVERCURLING

BACKGROUND OF THE INVENTION

1. Field of the Invention

The present invention relates to a process for gentle long-lasting shaping (permanent waving or uncurling) of human hair whereby the hair-shaping agent is rinsed off before the winding or the use of other fastening means or, in the case of uncurling, before combing.

2. Prior Art

The shaping of hair by the conventional permanent waving method is achieved in that prewashed and thus swollen, but not previously reduced, hair is bent under tension (tensile stress) by use of a shaping device, particularly a curler, and treated with the permanent wave reducing agent. The permanent wave agent is allowed to act on the wound hair for 3 to 30 min, depending on the hair shaping desired, until reshaping has taken place. After exposure of the hair to the permanent wave agent, excess reducing agent is removed with water or by use of an acidic rinse. Despite thorough rinsing, however, a small amount of reducing agent remains on the hair surface and inside the hair (for more details see SOFW Journal 123, pp. 79–83, 1997). After rinsing, the cystine disulfide bonds are reformed by use of a fixative, namely of an oxidant-containing agent.

In the conventional permanent waving method, as a rule, the hair-dresser determines the time of exposure to the reducing agent-containing shaping agent by assessing the degree of shaping with several test curlers. The hair-dresser is often uncertain and extends the exposure time to ensure adequate shaping. An excessively long exposure, however, results in an overtreatment of the hair, particularly along the hair shaft and at the hair tips. This is known as overcurling. It manifests itself, on the one hand, visually, in that the curls along the shaft and at the tip of the hair are very small (frizzing), and, on the other, in that the overcurled hair region feels limp despite the frizzing and shows inadequate elasticity. Such overcurling effects cause irreversible, permanent hair damage.

German Patent Application G8775 IVa/30h published on 10-4-1956 discloses a method for permanent shaping of keratin fibers whereby the keratin fibers, wound and exposed to a reactive reducing solution, are rinsed with water after a period of time that is insufficient for conventional shaping, and the fibers are then left on the curlers for 2 to 3.5 hours to expose them to air oxidation. The use of a chemical fixing agent is not required. This time-consuming and for the customer troublesome method has not been accepted by hair-dressers.

DE-A-36 10 394 discloses a process for shaping hair whereby the hair is treated at pH 6.0 to 7.5 with a hair-shaping shampoo containing from 1.5 to 12 wt % of at least one surfactant and from 2 to 15 wt % of at least one hair keratin-reducing substance. The hair is then rinsed with water, optionally wound onto curlers, optionally rinsed with water and then subjected to an oxidative aftertreatment.

Currently used shaping processes have in common the feature that the reducing permanent shaping agent acts on the hair in undiminished strength for a period of time required for hair shaping and thus, particularly after repeated hair shaping, causes irreversible hair damage, professionally referred to as "overcurling". The negative consequences for the hair are poor elasticity and springiness, reduced tensile strength, poor hair-styling properties and reduced sheen.

SUMMARY OF THE INVENTION

To reduce the afore-said overcurling effects, a new process was sought whereby the time of action of the chemical permanent wave agent on the hair would be markedly reduced and whereby the contact of the reducing agent with scalp would be limited to a minimum compared to conventional processes. As a result, the hair structure would be damaged to a lesser degree. Moreover, after removing the reducing agent, the residual thio compounds remaining inside the hair could also be utilized for hair shaping.

Surprisingly, we have now found that this objective can be reached by use of a process for shaping and volumizing hair characterized in that
a) an alkaline permanent shaping agent having pH 7.6 to 11 based on a hair keratin-reducing substance is applied to the hair,
b) the permanent shaping agent is allowed to act on the hair at room temperature for 5 to 30 min or at an elevated temperature for 2 to 20 min,
c) the hair is optionally rinsed with water,
d) the hair is treated with an acidic aqueous intermediate treatment agent having pH 2 to 6.5 and based on a salt, a betaine, an aliphatic organic acid and/or an aliphatic amino acid,
e) excess liquid is dabbed off the hair,
f) the hair is wound onto curlers, or some other shaping device or fastening means is used, or the hair is given a new shape in any other manner,
g) the hair is allowed to rest up to 30 min at room temperature or up to 20 min at an elevated temperature,
h) after step e) or step g), the hair is treated with an oxidant-based fixative,
i) the curlers or the other shaping or fastening means, if they were used, are removed, and
j) the fixative is removed from the hair by rinsing with water or by washing with a shampoo, and the hair is combed to obtain the desired hair style.

By the process according to the invention, the, preferably dry, hair is treated with a sufficient amount, for example 60 to 120 g, of a permanent hair shaping agent in the form of a liquid, cream or gel and based on a hair keratin-reducing substance. Particularly suitable creamy or gel-like permanent shaping agents are those which adhere well to dry hair. The permanent hair shaping agent is applied to the hair and reaches the inside of the hair in undiluted form. After a defined, short exposure time, the reducing phase can be interrupted without there being any hindering shaping devices on the entire head by rinsing the entire head with an acidic intermediate treating agent in the form of a rinse. In this manner, the reduced hair takes up water. The residual reducing agent remaining after rinsing is intentionally utilized for shaping and volumizing. The shaping process is promoted by two factors: The hair is arranged into the desired shape not only in a preswollen, but also in a prereduced condition.

Depending on the hair structure, the shaping and volumizing by the process described herein can be carried out in one step (reducing, rinsing, fixing and then winding) or two steps (reducing, rinsing, winding and then fixing). The novel process thus provides hair-dressers and customers with the advantage that individual requests can be met, particularly those referring to the hair structure, by reducing and fixing the hair by a one-step process or first reducing and then fixing by a two-step process.

Surprisingly, we have found that by the process according to the invention, particularly when thickened permanent hair shaping agents are used (cream, gel, paste), a more pronounced shaping effect can be achieved partly or completely, while using the same the exposure time as with liquid permanent hair shaping agents, on dry hair (unwashed, dry hair or washed and dried hair) rather than on moist hair as in the conventional waving process.

For uncurling, the hair can be given a new shape by combing rather than by use of (large) curlers. This embodiment of the process of the invention is characterized in that A) an alkaline permanent shaping agent in the form of a cream, gel or paste, based on a hair keratin-reducing substance and having a pH of 7.6 to 11, is applied to the hair,
B) the permanent shaping agent is allowed to act on the hair at room temperature for 5 to 30 min or at an elevated temperature for 2 to 20 min,
C) the hair is rinsed with water,
D) to the hair is applied an acidic aqueous intermediate treatment agent in the form of a cream, gel or paste having pH 2 to 6.5 and based on a salt, a betaine, an aliphatic organic acid and/or an aliphatic amino acid,
E) the hair is combed out (preferably 1 to 3 times),
F) the hair is allowed to rest up to 30 min at room temperature or up to 20 min at an elevated temperature,
G) the hair is treated with an oxidant-based fixative,
H) the fixative is removed from the hair by rinsing with water or by washing with a shampoo, and the hair is combed to obtain the desired hair style.

DETAILED DESCRIPTION OF THE INVENTION

Suitable hair keratin-reducing substances are all common substances of this kind. Useful are, in particular, thioglycolic acid, thioglycolamide, thiolactic acid, 3-mercaptopropionic acid, cysteine, cysteamine, alkyl- or acylcysteamine or the salts or mixtures of said compounds.

The hair keratin-reducing substance in the permanent hair shaping agent is present in an amount from 2 to 20 wt %, preferably from 4 to 13 wt % and particularly from 6 to 10 wt %. Besides the said and other, in themselves known, reducing agents, permanent hair-shaping agents usually contain an alkalizing substance the concentration of which depends on the kind and amount of the hair keratin-reducing substance. In particular, the permanent hair-shaping agents can have a pH from 3.5 to 10; they are preferably alkaline and thus contain as the alkalizing agent, namely the agent used for adjusting the pH, in particular, ammonia, sodium hydroxide or a water-soluble, physiologically tolerated organic base, for example diethanolamine or triethanolamine. The preferred alkalizing agent is ammonia. The pH is brought into the alkaline range from 7.1 to 11 and preferably from 7.5 to 9.5, depending on the hair keratin-reducing substance.

The permanent hair-shaping agent can be used in the form of an aqueous solution or emulsion or in thickened, water-based form, particularly as a cream, gel or paste. If the permanent hair-shaping agent is formulated as a cream, gel or paste, its viscosity is preferably in the range from 200 to 6000 mPa.s and particularly from 1000 to 5000 mPa.s, at 25° C. and at a shear rate of 12.9 $s^{-1}$.

Naturally, the permanent hair-shaping agent can contain all common additives known for such agents, for example thickeners, such as bentonite, fatty acids, starch, polyacrylic acid or derivatives thereof, cellulose derivatives, alginates, vaseline, paraffin oils; wetting agents or emulsions belonging to the classes of anionic, cationic, amphoteric or nonionic surface-active substances, for example fatty alcohol sulfates, fatty alcohol ether sulfates, alkylsulfonates, alkylbenzenesulfonates, quaternary ammonium salts, alkylbetaines, ethoxylated alkylphenols, fatty acid alkanolamides or ethoxylated fatty esters; furthermore opacifiers, for example polyethylene glycol esters; alcohols, for example ethanol, propanol, isopropanol and glycerol; sugars such as, for example, D-glucose; solubilizers, stabilizers, buffers, perfumes, dyes and hair-conditioning and hair-care constituents, for example cationic polymers, such as poly-dimethyidiallylammonium chloride (CTFA polyquaternium 6), polydimethyl- aminoethyl methacrylate (75% quaternized with diethyl sulfate, CTFA polyquaternium 11), CTFA polyquaternium 4, CTFA polyquaternium 5, CTFA polyquaternium 7, CTFA polyquaternium 9, CTFA polyquaternium 10, CTFA polyquaternium 14, CTFA polyquaternium 16, CTFA polyquaternium 22, lanolin derivatives, cholesterol, pantothenic acid and betaine.

The above-described additive ingredients are used in amounts common for such purposes, for example the wetting agents and emulsifiers at a total concentration of 0.2 to 30 wt %, the alcohols in a total amount from 0.1 to 20 wt %, the opacifiers, perfumes and dyes in an amount from 0.01 to 1 wt % each, the buffers in a total amount from 0.1 to 10 wt % and the sugars, solubilizers, stabilizers, hair conditioners and hair- care constituents in an amount from 0.1 to 5 wt % each, the thickeners and solubilizers together being present in said agent in a total amount from 0.5 to 20 wt %.

Moreover, for purposes of enhancing the efficacy of the permanent shaping agent, it is possible to add to it a swelling agent and penetrant, for example dipropylene glycol monomethyl ether, 2-pyrrolidone or imidazolidin-2-one in an amount from 1 to 30 wt %, and for prevention of hair overcurling a dithio compound, for example dithioglycolic acid, dithiolactic acid, a dithiol of said compounds or a salt thereof.

After a length of time that is insufficient for permanently shaping the hair, said time depending on the hair structure, the pH, the shaping efficacy of the shaping agent, and the use temperature which amounts to 5 to 30 min (preferably 7 to 15 min) at room temperature and 2 to 30 min (preferably 5 to 10 min) at an elevated temperature, the hair is rinsed with an aqueous acidic intermediate rinse as per process step d), or uncurling is accomplished by first rinsing the hair with water and then treating it with an aqueous acidic intermediate treating agent in the form of an aqueous cream, gel or paste as per process step D). When the intermediate treating agent is a cream, gel or paste, its viscosity is preferably in the range from 1000 to 500,000 mPa.s and particularly from 4000 to 50,000 mPa.s at 25° C. and at a shear rate of 12.9 $s^{-1}$.

The aqueous intermediate treating agent is acidic and preferably contains an aliphatic organic acid, particularly a physiologically tolerated acid selected from among citric, tartaric, lactic, acetic, glyoxylic, maleic and fumaric acid. These acids can be used alone or in admixture with each other in an amount from 0.05 to 3 wt %, depending on the amount of the aqueous intermediate treating agent to be used for the treatment, the pH preferably being from 2.0 to 5.0 and particularly from 2.5 to 4.5. The optionally present salt can be, besides a known physiologically tolerated inorganic or organic salt, for example NaCl or $Na_2SO_4$, also a salt of the aforesaid aliphatic organic acid or aliphatic amino acid.

The intermediate treating agent and the intermediate rinse can also contain hair-care or hair- conditioning components, for example cationic polymers such as, for example, those indicated in the foregoing as constituents of the permanent hair-shaping agent, or lanolin, lecithin, glycerol, allantoin, Purcellin oil, silicone oil, sperm oil, wool wax, paraffin oil, bees wax, urea, low-boiling paraffins, albumin-fatty acid condensate, keratin hydrolyzate, betaine, cholesterol or pantothenic acid. The hair- conditioning component, alone or in admixture, is contained in the aqueous intermediate treating agent in an amount from 0.1 to 5 wt %. Advantageously, the aqueous intermediate treating agent can also contain salts of multivalent metals, particularly of magnesium, calcium or aluminum, for example $MgCl_2$, $AlCl_3$ or $MgSO_4$, in an amount from 0.5 to 5 wt %.

When an acidic aqueous intermediary rinse is used as the intermediate treating agent, excess rinsing liquid is dabbed off the curlers, if necessary.

In a preferred embodiment of the process, the rinsed hair is divided into individual strands and wound onto curlers 5 to 30 millimeters and preferably 5 to 15 millimeters in diameter. Any other shaping device or fastening means can be used, for example corrugated films, spiral curlers or clips, for example those for curl paper.

For hair uncurling by the combing method (without fastening means), the hair is combed out one to three times with a coarse comb during a treatment period of 10 to 30 min at room temperature or up to 20 min, preferably 8 to 12 min, at an elevated temperature, and then subjected to oxidative aftertreatment ("fixing").

When fastening means are used, the hair is subjected to oxidative aftertreatment after it has rested on the fastening means for up to 30 min, preferably from 10 to 20 min, at room temperature or for up to 20 min, preferably from 8 to 12 min, at an elevated temperature.

The fixative is preferably used in an amount from 80 to 100 g, depending on hair fullness. For the oxidative aftertreatment in the wound or unwound state of the hair, any fixative suitable for such treatment can be used. Examples of oxidants that can be used in such fixatives are potassium and sodium bromate, sodium perborate, urea peroxide and hydrogen peroxide. The concentration of the oxidant varies depending on the use time (as a rule from 5 to 15 min) and the use temperature. Usually, the oxidant is present in the ready-for-use aqueous aftertreatment agent at a concentration from 0.5 to 10 wt %. The preferred fixative is a 0.5 to 5% aqueous solution of hydrogen peroxide. The oxidative aftertreatment agent can, of course, also contain other substances, for example wetting agents, hair-care agents such as cationic polymers, weak acids, buffers or peroxide stabilizers, and it can be in the form of an aqueous solution, an emulsion or in thickened, water-based form, particularly as a cream, gel or paste. In particular, these common additives can be present in the fixative in an amount from 0.1 to 10 wt %. Fixatives in the form of a cream, gel or paste preferably have a viscosity from 1000 to 6000 mPa.s and particularly from 1000 to 3000 mPa.s at 25° C. and at a shear rate of 12.9 $s^{-1}$.

In an alternative process variant involving the use of fastening means, the fixative is applied directly to the hair after the afore-described rinsing of the hair with an acidic aqueous intermediate rinse, and only then are the fastening means, for example curlers, put on. In this case, further use of a fixative following the winding and rest (step f) can be omitted.

The fastening means or rollers are then removed. If necessary, the wound hair can again be subjected to oxidative aftertreatment. The hair is then rinsed with water, optionally set to waves with water and then dried.

We have found that by use of the process according to the invention, an overcurling effect and the attendant hair damage can be prevented to a high degree.

By "elevated" temperature is meant a temperature from 35 to 60° C. and preferably 40 to 50° C. The elevated temperature can be achieved, for example, by use of a hair drier with or without a cover, or by use of an infrared heating device.

EXAMPLES

The following examples illustrate the invention more closely.

Example 1

Permanent Wave Process

A liquid alkaline permanent wave agent, pH=8.0, having the following composition was applied uniformly to 15-cm long dry hair (not previously washed with a shampoo) predamaged by color treatment:

| | |
|---|---|
| 15.2 wt % | of ammonium thioglycolate, 70% |
| 3.5 wt % | of ammonium hydrogen carbonate |
| 1.0 wt % | of ammonia, 25% |
| 0.8 wt % | of polydimethyldiallylammonium chloride |
| 1.5 wt % | of urea |
| 78.0 wt % | of water, demineralized |
| 100.00 wt % | |

The permanent wave agent had a viscosity of 2 mPa.s at 25° C. and at a shear rate of 12.9 $s^{-1}$.

After an exposure time of 8 min at an elevated temperature of 40° C. obtained by use of an infrared heater, the hair was rinsed with 500 mL of an acidic aqueous intermediate rinse, pH=2.6, having the following composition:

| | |
|---|---|
| 0.4 wt % | of lactic acid |
| 2.8 wt % | of magnesium sulfate |
| 2.0 wt % | of betaine |
| 94.8 wt % | of water |
| 100.00 wt % | |

(the intermediate rinse had a viscosity of 2 mPA.s at a shear rate of 12.9 $s^{-1}$ and 25° C.).

After the excess liquid was dabbed off, the hair was wound onto rollers having a diameter of 6 to 8 mm.

After a 10-min resting period at a temperature of 40° C. obtained by use of an infrared heater, the wound hair was subjected to oxidative aftertreatment with 150 mL of a 2.5% aqueous hydrogen peroxide solution. The rollers were then removed, and the hair was rinsed with water and dried.

As a result of this treatment, the hair had loose curls and more volume, good feel and good wet combability.

Example 2

An alkaline permanent wave agent, pH=8.6, having the following composition was applied to 1 5-cm long dry, not predamaged hair (not previously washed with a shampoo):

| | |
|---|---|
| 17.0 wt % | of ammonium thioglycolate, 70% |
| 3.4 wt % | of ammonium thiolactate, 70% |

| | |
|---|---|
| 1.8 wt % | of ammonia, 25% aqueous solution |
| 0.5 wt % | of polydimethyldiallylammonium chloride |
| 3.0 wt % | of urea |
| 1.5 wt % | of 1,2-propylene glycol |
| 72.8 wt % | of water |
| 100.00 wt % | |

After an exposure time of 8 min at an elevated temperature of 40° C. obtained by use of an infrared heater, the hair was rinsed with 500 mL of an acidic aqueous intermediate rinse, pH=2.8, having the following composition:

| | |
|---|---|
| 0.5 wt % | of citric acid |
| 0.5 wt % | of keratin hydrolyzate, quaternized |
| 0.6 wt % | of cetyltrimethylammonium chloride |
| 1.0 wt % | of dimethylcarboxymethyl coco fatty amidoammonium betaine (Rewoteric ® AM B 14) |
| 97.4 wt % | of water |
| 100.00 wt % | |

The hair was then treated as in Example 1.

As a result of this treatment, the hair had loose curls, more volume, good feel and good wet combability.

Example 3

An alkaline permanent wave cream, pH=8.3, having the following composition was applied to 15-cm long dry, not predamaged hair (not previously washed with a shampoo):

| | |
|---|---|
| 11.0 wt % | of ammonium thioglycolate, 70% |
| 0.4 wt % | of ammonia, 25% |
| 1.0 wt % | of ammonium hydrogen carbonate |
| 0.2 wt % | of tetrasodium etidronate (Turpinal ® 4 NL) |
| 5.8 wt % | of paraffin oil (mineral oil) |
| 8.2 wt % | of stearyl alcohol |
| 1.1 wt % | of stearic acid |
| 5.0 wt % | of lauryl alcohol polyglycol ether with 23 units of ethylene oxide [EO] |
| 0.4 wt % | of cellulose gum (Tylose ® CB 4000) |
| 66.9 wt % | of water |
| 100.00 wt % | |

Viscosity: 1500 to 4500 mPa.s (SV-DIN[DIN=German Industrial Standard]; step 5; 25° C.; shear rate 12.9 s$^{-1}$)

The hair was then treated as in Example 1.

As a result of this treatment, the hair appeared in large curls and had more volume, good feel and good wet combability.

Example 4

An alkaline permanent wave gel, pH=8.0, having the following composition was uniformly applied to 18-cm long dry, hair predamaged by color treatment (not previously washed with a shampoo):

| | |
|---|---|
| 10.0 wt % of ammonium thioglycolate, 70% | |
| 3.0 wt % of cysteine | |

| | |
|---|---|
| 0.3 wt % of ammonia, 25%) (pH = 8.0) | |
| 20.0 wt % of polyoxyethylene-polyoxypropylene block copolymer (CTFA poloxamer 407) | |
| 0.2 wt % of tetrasodium etidronate (Turpinal ® 4 NL) | |
| 66.5 wt % of water | |
| 100.00 wt % | |

Viscosity: 1000 to 3500 mPa.s (SV-DIN; step 5; 25° C.; shear rate 12.9 s$^{-1}$).

After an exposure time of 10 min at an elevated temperature of 40° C. obtained by use of an infrared heater, the hair was rinsed with 500 mL of an acidic aqueous intermediate rinse, pH=2.8, having the following composition:

| | |
|---|---|
| 0.5 wt % | of citric acid |
| 0.5 wt % | of keratin hydrolyzate, quaternized |
| 0.6 wt % | of cetyltrimethylammonium chloride |
| 1.0 wt % | of dimethylcarboxymethyl coco fatty amidoammonium betaine (Rewoteric ® AM B 14) |
| 97.4 wt % | of water |
| 100.00 wt % | |

(The intermediate rinse had a viscosity of 2 mPa.s at a shear rate of 12.9 s$^{-1}$ and 25° C.). The hair was then treated as in Example 1.

As a result of this treatment, the hair had loose curls, more volume, good feel and good wet combability.

Example 5

A liquid alkaline permanent wave cream, pH=8.4, having the following composition was uniformly applied to 15-cm long, dry hair predamaged by color treatment (and not previously washed with a shampoo):

| | |
|---|---|
| 7.0 wt % | of thioglycolic acid, 99% |
| 5.0 wt % | of ammonia, 25% |
| 4.0 wt % | of ammonium hydrogen carbonate |
| 3.0 wt % | of paraffin oil (mineral oil) |
| 2.0 wt % | of stearic acid |
| 9.0 wt % | of stearyl alcohol |
| 4.0 wt % | of cetyl alcohol polyethylene glycol ether (25.EO) |
| 1.0 wt % | of perfume |
| 65.0 wt % | of water |
| 100.00 wt % | |

Viscosity: 1500 to 4000 mPa.s (SV-DIN; stage 5; 25° C.; shear rate 12.0 s$^{-1}$).

After an exposure time of 15 min at an elevated temperature of 40° C. obtained by use of an infrared heater, the hair was rinsed with 500 mL of an acidic aqueous intermediate rinse, pH=2.6, having the following composition:

| | |
|---|---|
| 0.4 wt % | of lactic acid |
| 2.8 wt % | of magnesium sulfate |
| 2.0 wt % | of betaine |
| 94.8 wt % | of water |
| 100.00 wt % | |

(The intermediate rinse had a viscosity of 2 mPa.s at a shear rate of 12.9 s$^{-1}$ and 25° C.).

After dabbing off excess liquid, a cream fixative of the following composition, pH=2.5, was applied to the hair:

| | |
|---|---|
| 3.00 wt % | of hydrogen peroxide |
| 9.00 wt % | of stearyl alcohol |
| 2.50 wt % | of cetyl alcohol polyethylene glycol ether (25 EO) |
| 9.00 wt % | of paraffin oil (mineral oil) |
| 2.00 wt % | of pentanediol |
| 1.00 wt % | of potassium hydrogen phosphate |
| 0.25 wt % | of phosphoric acid, 85% |
| 73.25 wt % | of water |
| 100.00 wt % | |

Viscosity: 1500 to 4000 mPa.s (SV-DIN; step 5; 25° C.; shear rate 12.9 s$^{-1}$).

The hair was now wound onto rollers 6 to 8 mm in diameter.

After a resting period of 10 min at a temperature of 40° C. obtained by use of an infrared heater, the rollers were removed from the hair, and the hair was rinsed with water and dried.

As a result of this treatment, the hair had loose curls, more volume, good feel and good wet combability.

Example 6

Process For Uncurling Curly Hair 80 g of an alkaline permanent shaping cream, pH=9.2, having the following composition was uniformly applied to naturally curled 18-cm long dry hair (not previously washed with a shampoo):

| | |
|---|---|
| 9.0 wt % | of thioglycolic acid, 99% |
| 9.7 wt % | of ammonia, 25% |
| 10.0 wt % | of a mixture of cetyl alcohol and stearyl alcohol |
| 2.0 wt % | of cetyl alcohol polyethylene glycol ether (25 EO) |
| 0.5% | of perfume |
| 68.8 wt % | of water |
| 100.00 wt % | |

(viscosity: 3500 mPa.s at 25° C. and a shear rate of 12.9 s$^{-1}$).

After an exposure time of 15 min at room temperature, the hair was thoroughly rinsed with water after which excess liquid was dabbed off. Then, 80 g of an acidic intermediate treating agent in the form of a paste of the following composition, pH=2.2, was uniformly applied to the hair:

| | |
|---|---|
| 2.5 wt % | of lactic acid, 80% |
| 2.0 wt % | of magnesium sulfate |
| 15.0 wt % | of a mixture of cetyl alcohol and stearyl alcohol |
| 2.0 wt % | of cetyl polyethylene glycol ether (25 EO) |
| 15.0 wt % | of bentonite |
| 0.5 wt % | of perfume |
| 63.0 wt % | of water |
| 100.00 wt % | |

(viscosity: 26,000 mPA.s at 25° C. and a shear rate of 12.9 s$^{-1}$).

The hair was then combed out three times with a coarse comb.

After an exposure time of 10 min, a cream fixative of the following composition, pH=2.3, was applied to the hair and massaged in:

| | |
|---|---|
| 2.5 wt % | of hydrogen peroxide |
| 7.0 wt % | of a mixture of cetyl alcohol and stearyl alcohol |
| 2.0 wt % | of cetyl alcohol polyethylene glycol ether (25 EO) |
| 3.0 wt % | of petrolatum |
| 0.2 wt % | of disodium phosphate |
| 0.5 wt % | of perfume |
| 0.2 wt % | of phosphoric acid, 75% |
| 84.6 wt % | of water |
| 100.00 wt % | |

(viscosity: 2000 mPa.s at 25° C. and a shear rate of 12.9 s$^{-1}$).

After a resting period of 10 min at room temperature, the hair was rinsed with water and then dried.

As a result of this treatment, the hair was straightened out, and the originally tight curls were converted into loose curls as required by today's modern hair styling. Moreover, the hair was in good condition that manifested itself by good feel and good wet combability.

Example 7

Process For Uncurling Curly Hair 70 g of an alkaline permanent shaping agent in the form of a cream, pH=9.4, having the following composition was uniformly applied to naturally curled 15-cm long dry hair (not previously washed with a shampoo):

| | |
|---|---|
| 11.0 wt % | of thioglycolic acid, 99% |
| 13.2 wt % | of ammonia, 35% |
| 5.0 wt % | of a mixture of cetyl alcohol and stearyl alcohol |
| 1.0 wt % | of cetyl alcohol polyethylene glycol ether (25 EO) |
| 0.5 wt % | of perfume |
| 69.3 wt % | of water |
| 100.00 wt % | |

(viscosity: 1500 mPa.s at 25° C. and at a shear rate of 12.9 s$^{-1}$).

After an exposure time of 12 min at room temperature, the hair was thoroughly rinsed with water after which excess liquid was towelled off. Then, 70 g of an acidic intermediate treating agent in the form of a paste of the following composition, pH=2.1, was uniformly applied to the hair:

| | |
|---|---|
| 2.5 wt % | of lactic acid, 80% |
| 2.0 wt % | of magnesium sulfate |
| 15.0 wt % | of a mixture of cetyl alcohol and stearyl alcohol |
| 2.0 wt % | of cetyl polyethylene glycol ether (25 EO) |
| 0.5 wt % | of perfume |
| 78.0 wt % | of water |
| 100.00 wt % | |

(viscosity: 6000 mPa.s at 25° C. and at a shear rate of 12.9 s$^{-1}$).

The hair containing the paste was then combed out twice with a coarse comb.

After an exposure time of 10 min, a cream fixative of the following composition, pH=4.3, was applied to the hair:

| | |
|---|---|
| 11.0 wt % | of sodium bromate |
| 6.0 wt % | of a mixture of cetyl alcohol and stearyl alcohol |
| 2.0 wt % | of cetyl polyethylene glycol ether (25 EO) |
| 5.0 wt % | of petrolatum |
| 0.5 wt % | of sodium phosphate |
| 0.5 wt % | of a cationic polymer (CTFA polyquaternium 6) |
| 0.5 wt % | of perfume |
| 74.5 wt % | of water |
| 100.00 wt % | |

(viscosity: 2600 mPa.s at 25° C. and at a shear rate of 12.9 s$^{-1}$).

After a resting period of 10 min at room temperature, the hair was rinsed with water and then dried.

As a result of this treatment, the hair was straightened out, and the originally tight curls were converted into loose curls as required by today's modern hair styling. Moreover, the hair was in good condition that manifested itself by good feel and good wet combability.

What is claimed is:

1. A method of permanent shaping and volumizing hair, said method consisting of the steps of:
   a) providing an alkaline permanent shaping composition having a pH of 7.6 to 11 and comprising a hair keratin-reducing substance;
   b) applying the permanent shaping composition to the hair and allowing the permanent shaping composition to act on the hair for 5 to 30 minutes at room temperature or for 2 to 20 minutes at an elevated temperature of from 35 to 60° C.;
   c) providing an acidic aqueous intermediate treating agent having a pH of 2 to 6.5 and comprising an aliphatic organic acid;
   d) after the applying and the allowing of step b), applying the acidic aqueous intermediate treating agent to the hair and subsequently dabbing off any excess liquid present on the hair if necessary;
   e) after the applying and the dabbing of step d), winding the hair onto a shaping device or fastening means;
   f) after the winding of step e), allowing the hair to rest for up to 30 minutes at said room temperature or to rest up to 20 minutes at a raised temperature of from 35 to 60° C.;
   g) after step f), treating the hair with an oxidant-based fixative;
   h) removing the shaping device or fastening means from the hair; and
   i) then removing the fixative from the hair by rinsing with water, or washing out the fixative with a shampoo, and combing the hair to obtain a predetermined hair style.

2. A method of permanent shaping and volumizing hair, said method consisting of the steps of:
   a) providing an alkaline permanent shaping composition having a pH of 7.6 to 11 and comprising a hair keratin-reducing substance;
   b) applying the permanent shaping composition to the hair and allowing the permanent shaping composition to act on the hair for 5 to 30 minutes at room temperature or for 2 to 20 minutes at an elevated temperature of from 35 to 60° C.;
   c) providing an acidic aqueous intermediate treating agent having a pH of 2 to 6.5 and comprising an aliphatic organic acid;
   d) after the applying and the allowing of step b), rinsing the hair with water;
   e) after the rinsing of the hair with water in step d), applying the acidic aqueous intermediate treating agent to the hair and subsequently dabbing off any excess liquid present on the hair if necessary;
   f) after the applying and the dabbing of step e), winding the hair onto a shaping device or fastening means;
   g) after the winding of step f), allowing the hair to rest for up to 30 minutes at said room temperature or to rest up to 20 minutes at a raised temperature of from 35 to 60° C.;
   h) after step g), treating the hair with an oxidant-based fixative;
   i) removing the shaping device or fastening means from the hair; and
   j) then removing the fixative from the hair by rinsing with water, or washing out the fixative with a shampoo, and combing the hair to obtain a predetermined hair style.

3. The method as defined in claim 1 or 2, wherein said aliphatic organic acid is at least one acid ingredient selected from the group consisting of aliphatic amino acids, citric acid, tartaric acid, lactic acid, acetic acid, glyoxylic acid, maleic acid and fumaric acid.

4. The method as defined in claim 1 or 2, wherein said acidic aqueous intermediate treating agent includes betaine.

5. The method as defined in claim 1 or 2, wherein said acidic aqueous intermediate treating agent includes a physiologically compatible inorganic or organic salt.

6. The method as defined in claim 1 or 2, wherein said acidic aqueous intermediate treating agent includes at least one physiologically compatible inorganic or organic salt selected from the group consisting of sodium salts, magnesium salts, calcium salts and aluminum salts.

7. The method as defined in claim 1 or 2, wherein said acidic aqueous intermediate treating agent includes at least one hair care or hair conditioning ingredient.

8. The method as defined in claim 1 or 2, wherein the hair keratin reducing substance is at least one member selected from the group consisting of thioglycolic acid, cysteine, thiolactic acid, salts of thioglycolic acid, salts of cysteine and salts of thiolactic acid.

9. The method as defined in claim 1 or 2, wherein the permanent shaping composition is in the form of a gel, cream or paste.

10. The method as defined in claim 1 or 2, wherein the permanent shaping composition is allowed to act on the hair for 7 to 15 minutes at said room temperature.

11. The method as defined in claim 1 or 2, wherein said elevated temperature is from 40 to 50° C. and said permanent shaping composition is allowed to act on the hair for 5 to 10 minutes at said elevated temperature.

12. The method as defined in claim 1 or 2, wherein said permanent shaping composition has a viscosity in a range from 200 to 6000 mPa.s at a shear rate of 12.9$^{-1}$ at 25° C.

13. The method as defined in claim 1 or 2, wherein said shaping device or fastening means comprises curlers.

14. The method as defined in claim 1 or 2, wherein said oxidant-based fixative is an aqueous solution of hydrogen peroxide.

15. The method as defined in claim 1 or 2, wherein the hair to which said permanent shaping agent is applied has not been washed immediately prior to the applying of said permanent shaping agent.

16. The method as defined in claim 1 or 2, wherein said acidic aqueous intermediate treating agent is allowed to act on the hair at said room temperature for from 10 to 30 minutes or at said raised temperature for from 8 to 12 minutes.

17. A method of permanent shaping and volumizing hair, said method consisting of the steps of:
   a) providing an alkaline permanent shaping composition having a pH of 7.6 to 11 and comprising a hair keratin-reducing substance;
   b) applying the permanent shaping composition to the hair and allowing the permanent shaping composition to act on the hair for 5 to 30 minutes at room temperature or for 2 to 20 minutes at an elevated temperature of from 35 to 60° C.;
   c) rinsing the hair with water after the applying and the allowing of step b);
   d) providing an acidic aqueous intermediate treating agent in the form of a cream, gel or paste, having a pH of 2 to 6.5 and comprising an aliphatic organic acid;
   e) after the rinsing of the hair with water in step c), applying the acidic aqueous intermediate treating agent to the hair;
   f) combing the hair out;
   g) after the applying of the acidic aqueous intermediate treating agent in step e), allowing the hair to rest for up to 30 minutes at said room temperature or for up to 20 minutes at a raised temperature of from 35 to 60° C.;
   h) after the applying of step g), treating the hair with an oxidant-based fixative; and
   i) subsequently removing the fixative from the hair by rinsing with water, or washing out the fixative with a shampoo, and combing the hair to obtain a predetermined hair style.

18. The method as defined in claim 17, wherein said aliphatic organic acid is at least one acid ingredient selected from the group consisting of aliphatic amino acids, citric acid, tartaric acid, lactic acid, acetic acid, glyoxylic acid, maleic acid and fumaric acid.

19. The method as defined in claim 17, wherein said acidic aqueous intermediate treating agent includes betaine.

20. The method as defined in claim 17, wherein said acidic aqueous intermediate treating agent includes a physiologically compatible inorganic or organic salt.

21. The method as defined in claim 20, wherein said salt is selected from the group consisting of salts of sodium, magnesium, calcium or aluminum.

22. The method as defined in claim 17, wherein said acidic aqueous intermediate treating agent includes at least one hair care or hair conditioning ingredient.

23. The method as defined in claim 17, wherein the hair keratin reducing substance is at least one member selected from the group consisting of thioglycolic acid, cysteine, thiolactic acid, salts of thioglycolic acid, salts of cysteine and salts of thiolactic acid.

24. The method as defined in claim 17, wherein the permanent shaping composition is in the form of a gel, cream or paste.

25. The method as defined in claim 17, wherein the permanent shaping composition is allowed to act on the hair for 7 to 15 minutes at said room temperature.

26. The method as defined in claim 17, wherein said elevated temperature is from 40 to 50° C. and said permanent shaping composition is allowed to act on the hair for 5 to 10 minutes at said elevated temperature.

27. The method as defined in claim 17, wherein said permanent shaping composition has a viscosity in a range from 200 to 6000 mPa.s at a shear rate of $12.9^{-1}$ at 25° C.

28. The method as defined in claim 17, wherein said acidic aqueous intermediate treating agent has a viscosity in a range from 4000 to 50,000 mPa.s at a shear rate of $12.9^{-1}$ at 25° C.

29. The method as defined in claim 17, wherein said oxidant-based fixative is an aqueous solution of hydrogen peroxide.

30. The method as defined in claim 17, wherein the hair to which said permanent shaping agent is applied has not been washed immediately prior to the applying of said permanent shaping agent.

* * * * *